United States Patent
Coppens et al.

(10) Patent No.: US 10,166,160 B2
(45) Date of Patent: Jan. 1, 2019

(54) AIR BEARING DEVICE AND METHOD FOR TRANSFERRING PATIENTS

(71) Applicant: Qfix Systems, LLC, Avondale, PA (US)

(72) Inventors: Daniel D. Coppens, Avondale, PA (US); David M. Rabeno, Avondale, PA (US); Richard J. Herrschaft, West Chester, PA (US); John R. Capone, West Chester, PA (US)

(73) Assignee: QFIX SYSTEMS, LLC, Avondale, PA (US)

( * ) Notice: Subject to any disclaimer, the term of this patent is extended or adjusted under 35 U.S.C. 154(b) by 0 days.

(21) Appl. No.: 13/773,547

(22) Filed: Feb. 21, 2013

(65) Prior Publication Data

US 2013/0212806 A1   Aug. 22, 2013

Related U.S. Application Data

(60) Provisional application No. 61/601,191, filed on Feb. 21, 2012.

(51) Int. Cl.
*A61G 7/10* (2006.01)
*A61B 6/04* (2006.01)
*A47C 31/02* (2006.01)
*A61B 5/055* (2006.01)

(52) U.S. Cl.
CPC .......... *A61G 7/1028* (2013.01); *A47C 31/023* (2013.01); *A61B 5/0555* (2013.01); *A61B 6/0407* (2013.01); *A61G 7/1026* (2013.01)

(58) Field of Classification Search
CPC .. A61G 7/1025; A61G 7/1026; A61G 7/1028; A47C 27/085; A47C 27/087; A47C 31/023; A61B 5/0555; A61B 6/0407
USPC ......... 5/81.1 R, 81.1 HS, 706, 710–715, 731
See application file for complete search history.

(56) References Cited

U.S. PATENT DOCUMENTS

| | | | | |
|---|---|---|---|---|
| 3,416,626 A * | 12/1968 | Nagamatsu | .................... | 180/124 |
| 3,644,950 A * | 2/1972 | Lindsay, Jr. | ........... | A61G 7/057 |
| | | | | 297/DIG. 3 |
| 3,667,073 A * | 6/1972 | Renfroe | ....................... | 5/81.1 R |
| 3,739,407 A * | 6/1973 | Stiller | .......................... | 5/81.1 R |
| 3,778,851 A * | 12/1973 | Howorth | .......................... | 5/423 |
| 4,272,856 A * | 6/1981 | Wegener et al. | ............ | 5/81.1 T |
| 4,417,639 A * | 11/1983 | Wegener | ....................... | 180/125 |
| 4,528,704 A * | 7/1985 | Wegener et al. | ............ | 5/81.1 R |
| 4,686,719 A * | 8/1987 | Johnson et al. | ............. | 5/81.1 R |
| 4,805,626 A * | 2/1989 | DiMassimo et al. | ......... | 600/415 |
| 4,896,389 A * | 1/1990 | Chamberland | .... | A61G 7/05784 |
| | | | | 5/710 |
| 5,065,464 A * | 11/1991 | Blanchard et al. | .......... | 5/81.1 R |
| 5,067,189 A * | 11/1991 | Weedling et al. | ........... | 5/81.1 R |
| 5,129,765 A * | 7/1992 | Smith et al. | .................... | 406/86 |
| 5,483,709 A * | 1/1996 | Foster et al. | ................. | 5/81.1 R |

(Continued)

*Primary Examiner* — Robert G Santos
*Assistant Examiner* — David R Hare
(74) *Attorney, Agent, or Firm* — RatnerPrestia

(57) ABSTRACT

The present invention provides a low friction device for transferring patients from one surface to another. This system allows a patient to be immobilized on one supporting surface. The immobilized patient can then be transferred laterally onto the target modality using an air bearing that is thin, homogeneously radiolucent and compatible with a variety of diagnostic imaging and treatment modalities.

31 Claims, 12 Drawing Sheets

(56) References Cited

U.S. PATENT DOCUMENTS

| | | | |
|---|---|---|---|
| RE35,299 E * | 7/1996 | Weedling et al. | 5/81.1 T |
| 6,016,582 A * | 1/2000 | Larson | 5/691 |
| 6,467,106 B1 * | 10/2002 | Heimbrock | 5/81.1 C |
| 6,701,544 B2 * | 3/2004 | Heimbrock | 5/81.1 R |
| 6,775,868 B1 * | 8/2004 | Mileti | A47C 27/001 |
| | | | 5/710 |
| 7,065,815 B2 * | 6/2006 | Buchanan | 5/691 |
| 7,146,660 B2 * | 12/2006 | Heimbrock | 5/81.1 R |
| 7,228,579 B2 | 6/2007 | Tidwell | |
| 7,725,963 B2 * | 6/2010 | Johnson | 5/81.1 R |
| 7,735,164 B1 * | 6/2010 | Patrick | 5/81.1 HS |
| 8,006,333 B2 * | 8/2011 | Genaro et al. | 5/615 |
| 8,276,222 B1 * | 10/2012 | Patrick | 5/81.1 HS |
| 8,302,222 B2 * | 11/2012 | Jasani | 5/81.1 R |
| 8,387,177 B2 * | 3/2013 | Davis | 5/81.1 R |
| 8,640,279 B2 | 2/2014 | Koger et al. | |
| 2005/0262638 A1 * | 12/2005 | Libunao | 5/710 |
| 2006/0000016 A1 * | 1/2006 | Weedling et al. | 5/81.1 HS |
| 2011/0277234 A1 * | 11/2011 | Jasani | 5/81.1 R |
| 2012/0304384 A1 * | 12/2012 | Scholz et al. | 5/600 |
| 2012/0317713 A1 * | 12/2012 | Eytan et al. | 5/81.1 R |
| 2015/0143628 A1 * | 5/2015 | Fowler et al. | 5/81.1 T |

\* cited by examiner

AIR BEARING DEVICE AND METHOD FOR TRANSFERRING PATIENTS

CROSS REFERENCE TO RELATED APPLICATION

The present application claims priority from U.S. Provisional Application Ser. No. 61/601,191, filed on 21 Feb. 2012.

FIELD OF THE INVENTION

This invention relates to devices designed for positioning, transportation, and treatment of patients for radiation therapy and diagnostic imaging. Specifically, the present invention relates to devices for moving positioned or immobilized patients via a low friction interface to allow transfer of the patient from a trolley to a variety of target modalities.

BACKGROUND OF THE INVENTION

Radiation therapy and diagnostic imaging equipment are used frequently in hospitals and treatment centers. Modern techniques for radiation therapy and diagnostic imaging require that patients be positioned and immobilized precisely. Generally, treatment of a tumor by radiation therapy is preceded by a diagnostic imaging procedure called simulation. During simulation, the patient is positioned in the manner anticipated for treatment. This includes the physical orientation of the patient using the positioning and immobilization devices that will be used in treatment. In this manner, the computer data set of the patient (DICOM) contains an accurate representation of the location of the tumor. That data set is then imported into treatment planning software (TPS) so that the treatment can be modeled and planned. It is critical that the patient be simulated in precisely the same position on the same devices as will be used in treatment to ensure accurate tumor location identification for treatment. Accurate tumor location and treatment spares the surrounding healthy tissue.

This patient positioning and immobilization process can be extensive and time consuming. It is beneficial, therefore, to set up the patient beforehand on a device other than the actual treatment or imaging device to better utilize time on the treatment or imaging equipment. In some cases imaging and treatment are done on the same day. In these cases it is beneficial to set up the patient once and have them remain immobilized throughout the imaging and treatment procedures.

When transporting patients from one piece of equipment to another, it is highly desirable to employ a low friction transfer system. Such a device enables the safe and efficient transfer of a patient from one target modality to another. By placing an air bearing between the patient support surface and supporting structure (e.g. CT couch, Linear accelerator couch, trolley), the patient can be moved easily and safely. An easy and safe transfer is beneficial for both the patient and the operator moving the patient.

Existing air bearing technologies suffer in that they either raise the patient surface too high when inflated or they are not uniformly radiolucent. By inflating a large area, existing systems cause a series of problems; they take up too much height which limits patient access to machines, they jostle the patient causing inaccuracies to occur in the patient's position, and they are unstable causing them to be unsafe and uncomfortable for the patient. The lack of uniformity or homogeneity under x-ray means that x-ray artifacting occurs when images are taken of the patient. Lack of uniformity can also hinder or make it impossible to treat through the system with high-energy x-radiation (such as linear accelerators) or particle beam radiation (such as proton therapy). Extremely low attenuation and homogeneity is required for transport systems to work properly in these environments.

A desirable low friction transfer system must be compatible with a variety of imaging and treatment modalities. It is also beneficial to use the same devices for radiation treatment and diagnostic imaging. By using the same device, hospitals and treatment centers can have better utilization of equipment and higher patient throughput. This in turn lowers cost and provides faster patient care.

SUMMARY OF THE INVENTION

The present invention solves the aforementioned problems and provides a low profile air bearing device that is uniformly radiolucent. Furthermore, the present invention makes efficient use of treatment equipment by enabling setup of the patient on the positioning or immobilization device in a separate room thereby leaving the treatment equipment free until needed. It also provides a means to use the same device for imaging and radiation therapy by providing a low friction surface between the immobilization device and the equipment. The patient can then be transferred from the setup table to a transport device, such as a trolley. The patient can then be moved from the trolley to the imaging equipment, then back to the trolley, then onto the treatment equipment and only require one patient setup.

The present invention provides a low friction interface comprised of an air bearing that is thin, presents very low attenuation to x-rays and has homogeneous x-ray attenuation. Such a configuration eliminates x-ray artifacts allowing the combination of bearing and patient transfer surface to be compatible with a variety of diagnostic imaging and treatment modalities. It can be constructed from materials that are compatible with modern MRI imaging machines. The air bearing is also detachable from the bottom of the patient transport surface so that it may be easily replaced due to wear, contamination or other reasons. When attached to the bottom surface of a homogeneous patient surface that is radiolucent, non-artifacting, MRI compatible or proton therapy compatible, this bearing design does not compromise any of these features.

Specifically, the present invention provides an air bearing bladder which creates a low friction interface between a supporting surface and a patient surface comprising: a top sheet and bottom sheet which do not separate by more than 15 mm while inflated under pressure and are constructed of substantially homogeneous and low x-ray attenuating material such that they exhibit an aluminum equivalence of less than 1.0 mm with a variation of less than +/−0.25 mm, and are sealed along their outer perimeter; at least one section of the bottom sheet which is gas permeable; and at least one air inlet.

The present invention also provides a method for moving patients relative to a support structure using the air bladder system of the present invention.

DETAILED DESCRIPTION OF THE INVENTION

Figure 1:
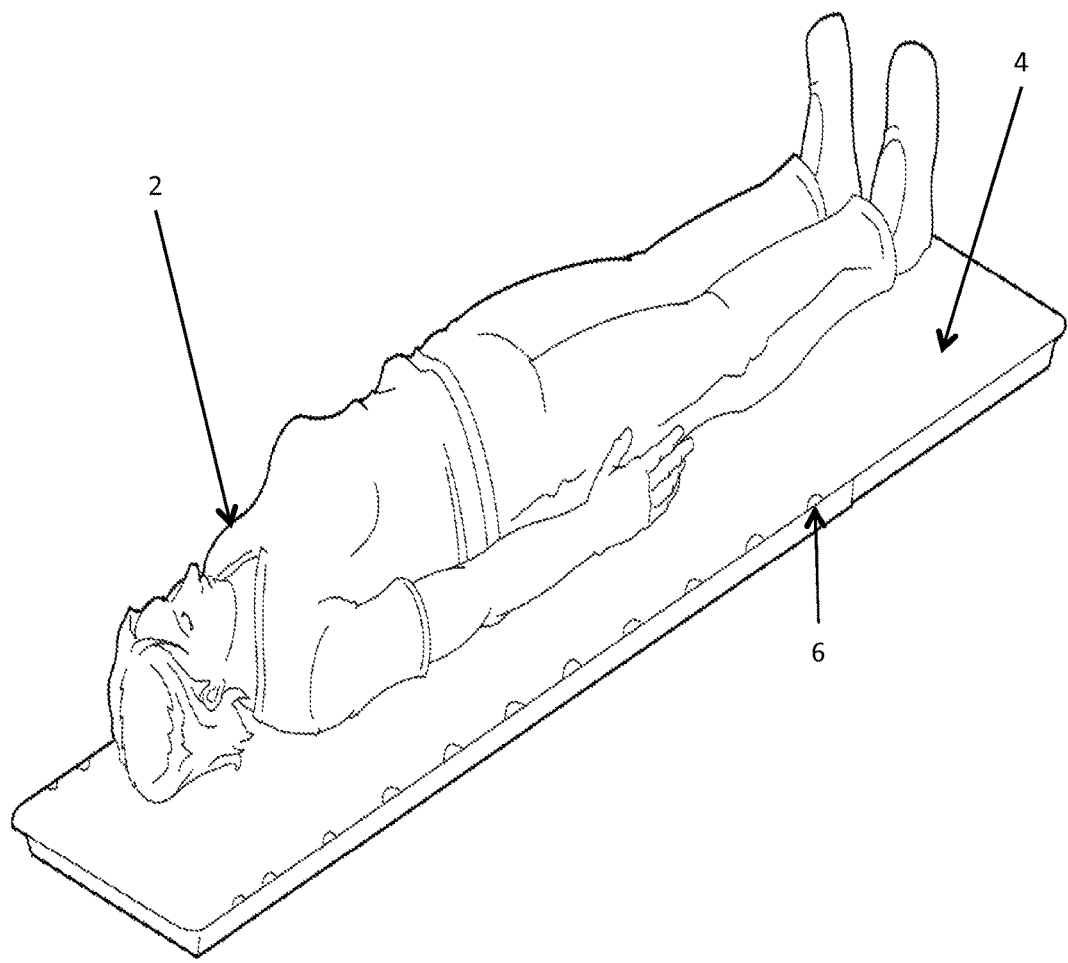
FIG. 1 is a top isometric view of a patient lying on a typical patient support surface with an air bearing bladder attached to the bottom of the support surface with tabs.

The present invention provides a low friction device for transferring patients from one surface to another. As seen in FIG. 1 this system allows a patient 2 to be positioned on one supporting surface 4, in this case shown with indexing notches 6 used for positioning accessories for radiation therapy. The patient can then be transferred onto the target modality.

Figure 2:
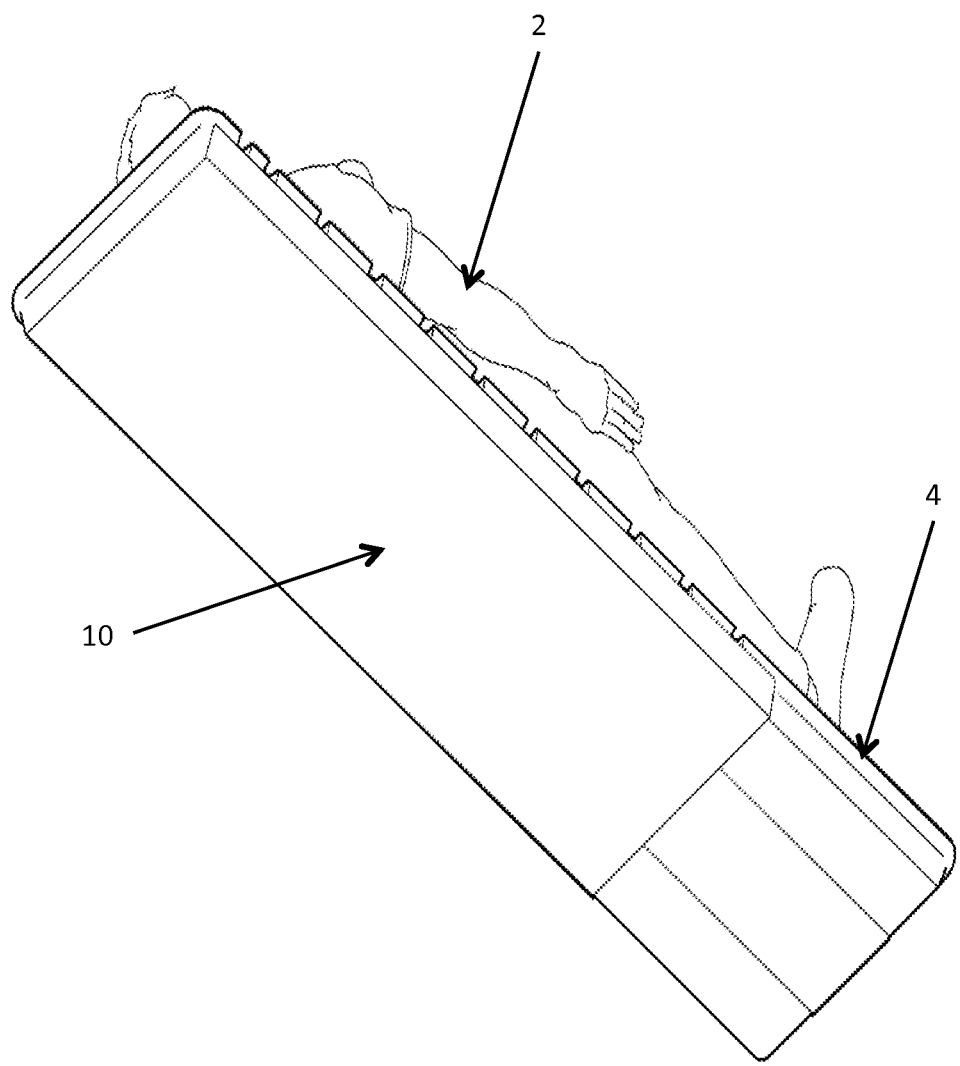
FIG. 2 is a bottom isometric view of a patient lying on a typical patient support surface with an air bearing bladder attached to the bottom of the support surface with tabs.
Figure 3:
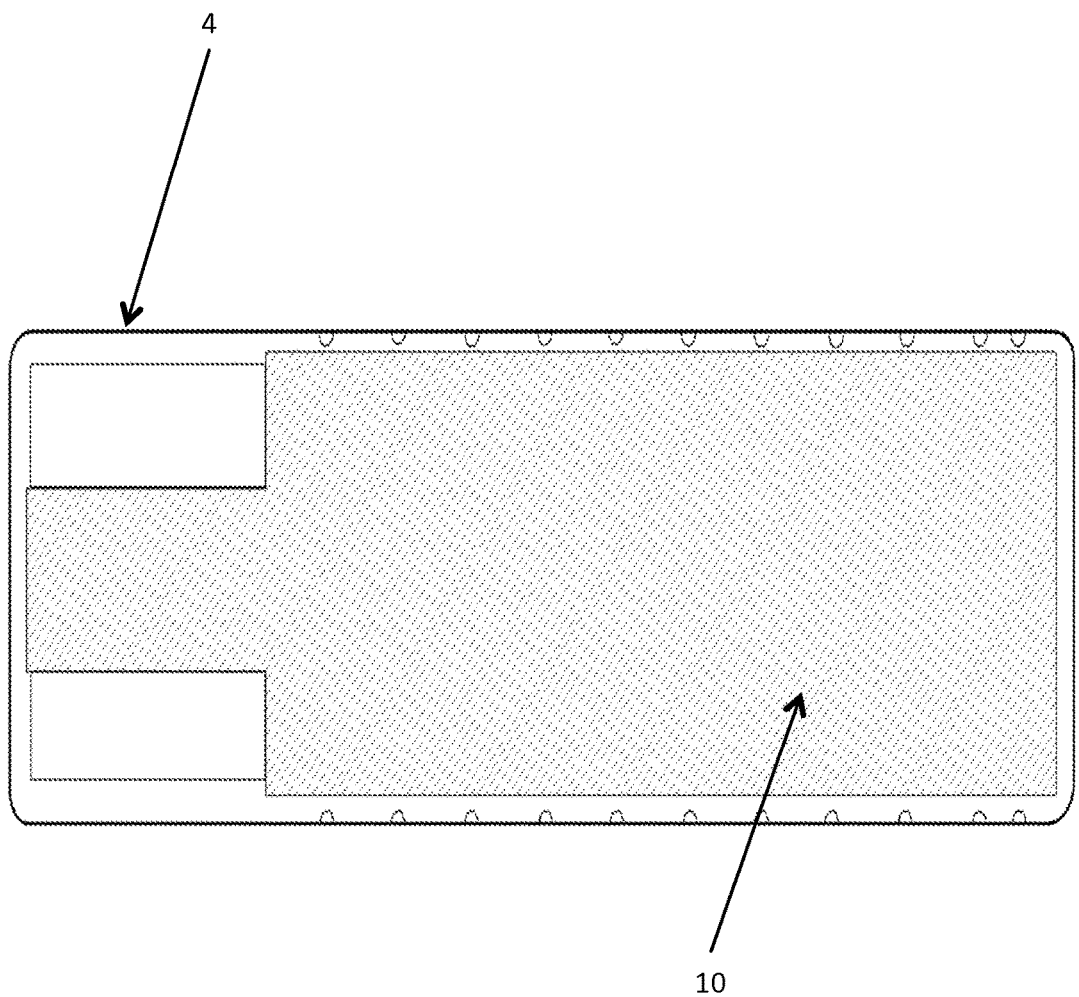
FIG. 3 is a bottom view of a typical patient support surface with an air bearing bladder attached to the bottom of the support surface with tabs.
Figure 4:
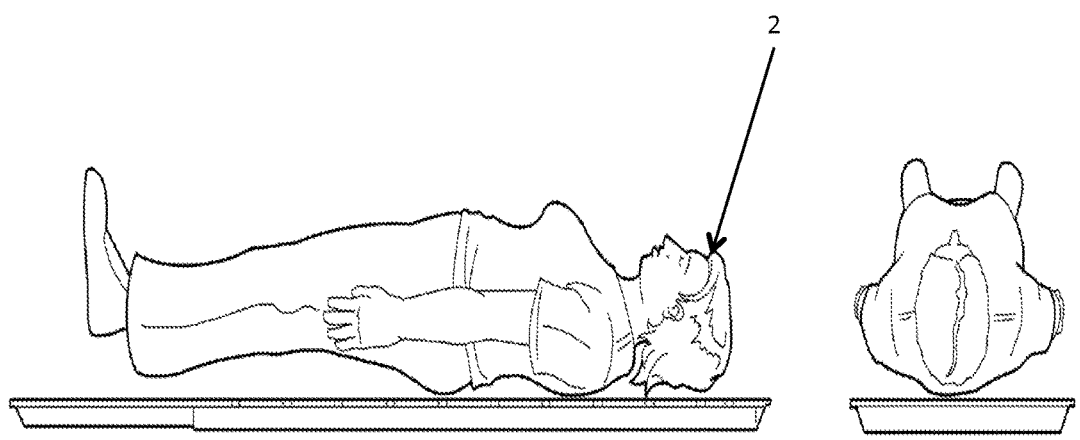
FIG. 4 is a side view of a patient lying on a typical patient surface with an air bearing attached to the bottom of the support surface with tabs.

FIG. 2 shows that the invention solves the problems of incorporating a low friction transfer device that is homogeneous to x-ray by providing an extremely thin air bladder 10 with a pressurized air source and multiple air holes in the bladder to allow pressurized air to escape. The bladder collapses flat with little to no wrinkling or folding when air pressure is removed. This feature contributes to the x-ray homogeneity of the design.

Figure 7:
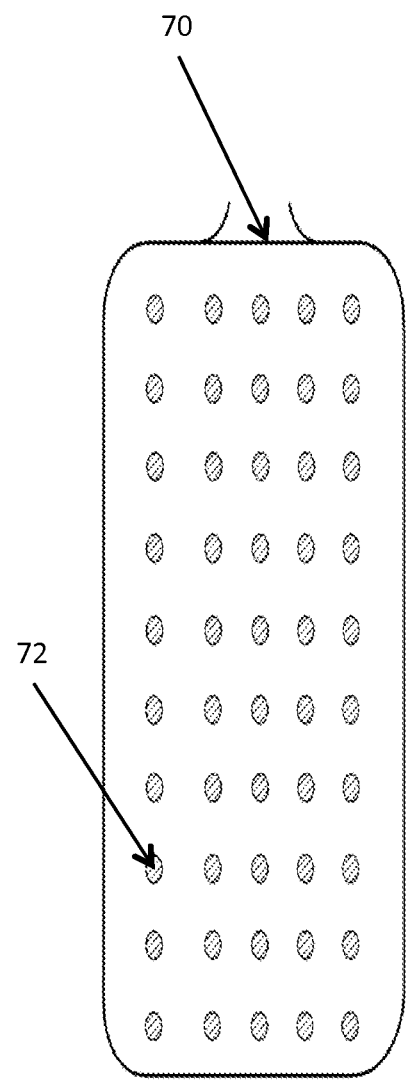
FIG. 7 illustrates a gas inlet and weld points connecting the solid face to the perforated face.
Figure 8:
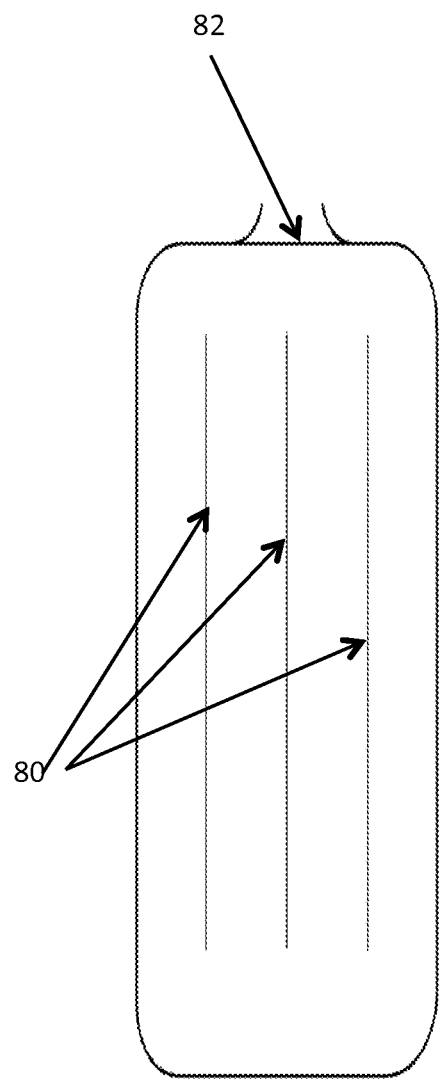
FIG. 8 illustrates a gas inlet and weld lines connecting the solid face to the perforated face.

X-ray attenuation in diagnostic imaging is generally characterized in equivalent thickness of aluminum (aluminum equivalence). Per IEC standards, this measurement is taken at 100 kVp with a half value layer (HVL) of 3.7 mm. In a preferred embodiment, shown in FIG. 5, the bladder is comprised of a fabric top skin 52 and a fabric bottom skin 54, each coated on one side with a thin layer of thermoplastic. The two thermoplastic layers are placed back to back such that they can be welded to each other 56. The perimeter is welded together, forming an airtight seal. The pressurizing air can be introduced through one of the skins (preferably the top skin) or through an edge penetration 70 (82 in FIG. 8). Shown in FIG. 7 additional spots 72 or as shown in FIG. 8 lines 80 are welded inside the perimeter to control the expansion of the bladder and to control airflow. The bladder remains thin while under pressure, which is highly advantageous for maintaining positional accuracy and safety during use.

Figure 5:
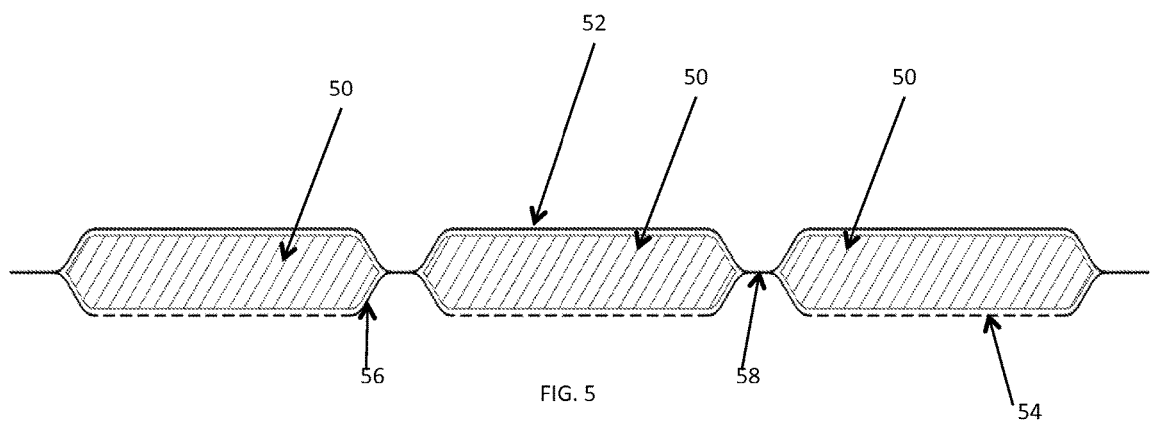
FIG. 5 illustrates a preferred embodiment using a solid face, a porous media, and a perforated face.

In a preferred embodiment, shown in FIG. 5, the air bladder can be filled with a thin homogeneous gas distribution medium 50 (e.g. a non-woven fabric) through which the air can travel. Without this medium the bladder can pinch off, restricting or shutting off airflow, thus reducing performance and reliability. While the distribution medium must be of a smaller size than the bladder such that it is contained inside the perimeter, welds 58 are formed for internal bladder control by welding directly through the distribution medium. This means that the amount of material through which a radiation beam must pass is always constant, even if the material is compressed in the welded areas. This provides the homogeneity and consistent attenuation required for the desired application. The bottom of the bladder contains multiple small holes 54. Air is introduced into the air bladder under pressure thereby filling the bladder. As the air is introduced into the bladder, the bladder expands while the air continually flows through the air holes in the bottom of the bladder. The flow of air through the air holes enables the patient transfer device to "float" on a cushion of air.

When the pressurized air source is removed, the bladder collapses to a substantially constant thickness providing a uniform radiation cross-section. The bladder can be attached to the bottom of a transport/treatment structure. Alternatively, one side of the bladder can function as the bottom of the structure. In a preferred embodiment, the bladder is removeably attached to the bottom of the structure so that it may be replaced if damaged.

In a preferred embodiment, the air bearing bladder consists of faces made of nylon fabric coated with thermoplastic polyurethane. With the polyurethane surfaces facing toward each other, this material can be welded together by conventional plastic welding technologies. In a preferred embodiment, a layer of thin non-woven material (such as a 4 oz breather or thinner) can be placed between the faces. And when thin enough, the connections between the top and bottom faces can be welded directly through the breather fusing the polyurethane layers to each other by melting through the breather or by melting the breather. This provides an excellent way to produce a very thin structure that is homogeneous to x-rays and completely flat when not inflated by air. When air flows through the bladder, it remains extremely thin because the top and bottom surfaces are welded together at various places.

Figure 6:
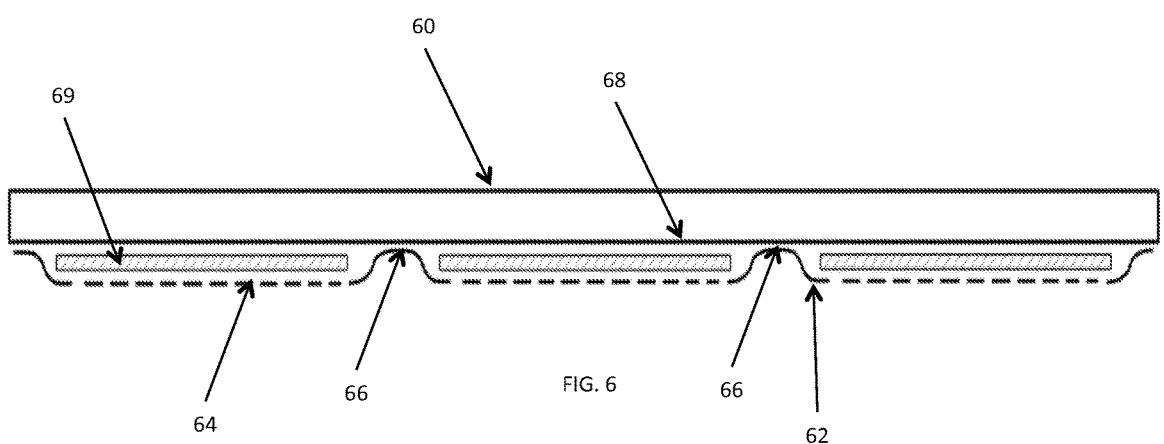
FIG. 6 illustrates a preferred embodiment using a rigid solid face a porous media and a perforated face.

Shown in FIG. 6 is another preferred embodiment in which the top of the air bladder 68 is formed from the bottom of the patient surface 60. The bottom sheet 62 contains perforations 64 and a layer of distribution medium 69 is located between the top and bottom layers.

One or more air bearing bladders can be attached to the bottom surface of a patient transfer surface. An air bearing can be fabricated that substantially covers the bottom surface of the transport surface or one or more smaller air bearings can be placed selectively on the bottom surface. In a preferred embodiment, however, for most applications, it is desirable that a single bladder cover the entire area that may be subjected to imaging and/or treatment. This way, the radiation attenuation remains constant and artifacting is minimized.

The target device can be many different types of equipment, including but not limited to; radiation therapy treatment tables, CT tables, MRI tables, brachytherapy tables, etc.

Air can be supplied for the air bearing using a number of methods such as a typical blower side of a vacuum (such as industrial blower, Shop-vac® or Nilfisk® unit). Hospital room supply air can also be used.

Figure 10:
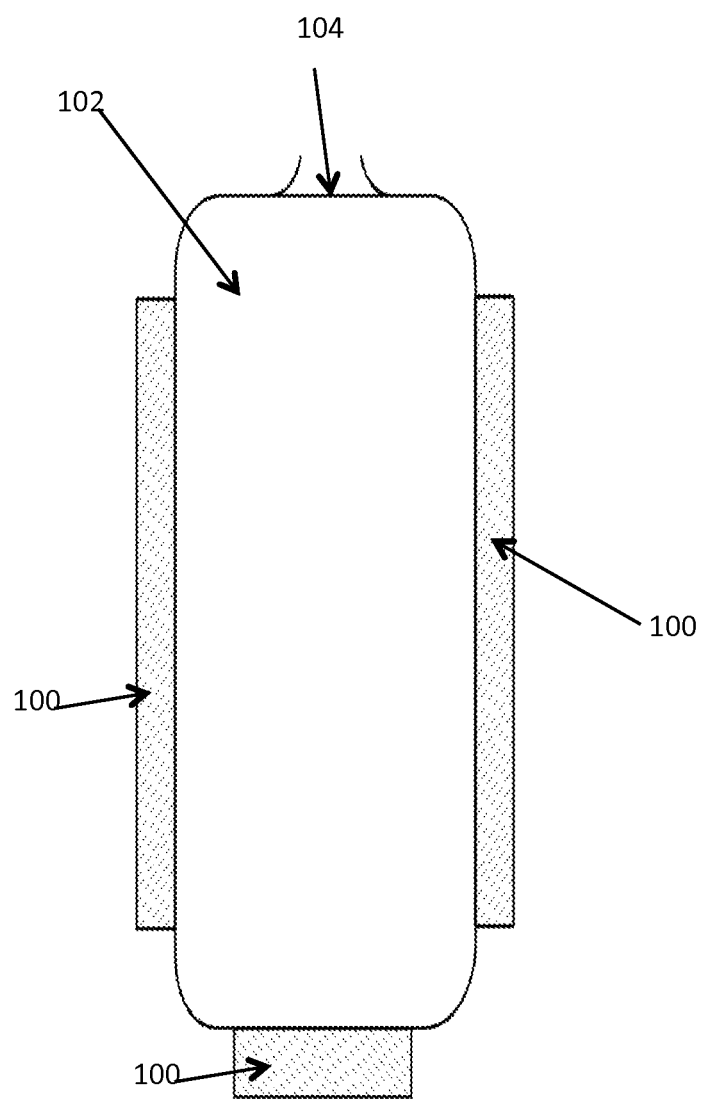
FIG. 10 is a view of an air bladder with means to attach the air cushion to the bottom of a device using tabs that extend from the edges.

As shown in FIG. 10 it is desirable to place tabs 100 around the edge of the air bladder 102. This allows the bladder to be attached to the transport surface. The tabs can be attached up the sides of the transport surface so that when the surface is slid from the trolley to the target modality and back, the potential for the edge of the bladder to be caught and torn from the surface is minimized.

In a preferred embodiment, the tabs are sealed from the air chamber so that they cannot inflate. The tabs can be attached to the transport surface with VHB® (Very High Bond) adhesive, VELCRO® or other standard means such as elastic bands or buttons. This provides a method to securely attach the bladder while making it possible to remove and replace. The bladder material may be coated with a low friction coating (silicone, TEFLON® or other) to reduce friction and improve sliding, reducing the effort required of the clinician to move the patient.

Figure 9:
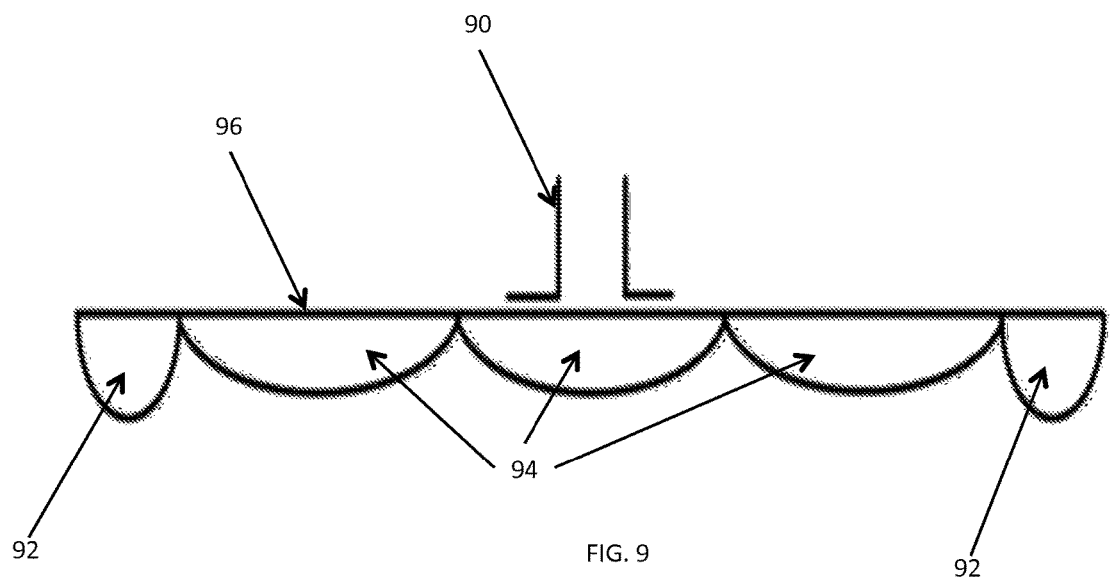
FIG. 9 illustrates outer regions that are taller in height when inflated than inner regions in height when inflated. By perforating only the inner regions, and leaving the outer regions solid, a hovercraft effect can be created. The outer region acts as the skirt while the inner region floods the center with air.

The top and bottom face-sheets of the bladder can be welded together in multiple places to limit the ability of the bladder to billow and rise. This configuration is shown in FIG. 9. By designing the bladder such that the perimeter regions 92 are taller than the internal regions 94, stability can be increased. FIG. 9 also shows that the top sheet 96 is constructed of a rigid composite sheet. The flexible polymer bottom sheet is attached directly to this rigid sheet.

Figure 11:
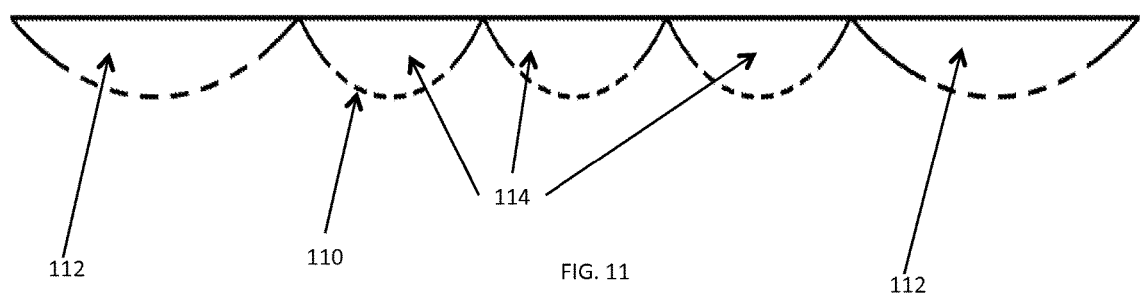
FIG. 11 is a cross section of the air bladder in which the perimeter regions are wider than are the internal regions.

In FIG. 11 the perimeter regions 112 are wider than the internal regions 114. This can be done to increase the stability of the device. All regions contain bottom perforations 110.

Figure 12:
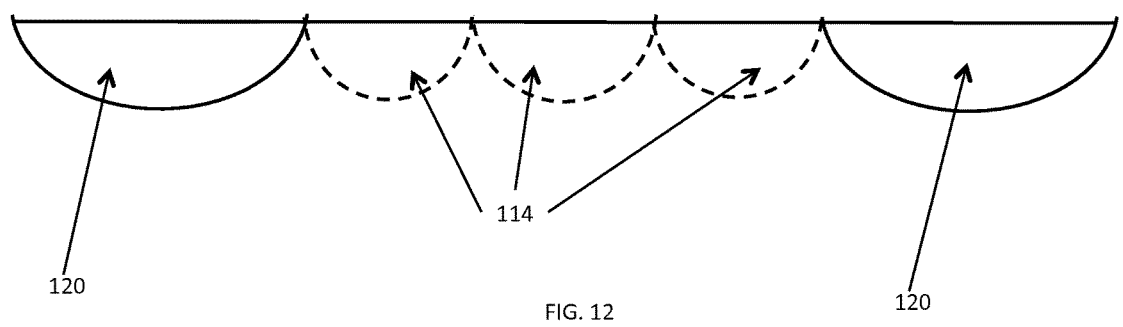
FIG. 12 is a cross section of the air bladder in which the bottom sheet does not contain perforations in the outer region.

FIG. 12 shows a preferred embodiment in which the bottom sheet 122 does not contain perforations in the outer region 120.

The present invention is further defined by the following claims.

We claim:

1. A patient transfer device, comprising:
a gas bearing bladder, the gas bearing bladder including:
  a top sheet and a bottom sheet sealed to one another along their outer perimeter relative to each other to form the gas bearing bladder, at least one of the top sheet and the bottom sheet being formed from a flexible material,
  at least one of spot connections or line connections connecting the top sheet and the bottom sheet, the spot connections or line connections being located inside the outer perimeter, and
  at least one gas inlet,
  wherein at least one section of the bottom sheet is gas permeable; and
a patient surface coupled to the gas bearing bladder such that a perimeter of the gas bearing bladder does not extend beyond a perimeter of the patient surface, the patient surface being configured and dimensioned to support a patient thereon, wherein the patient surface is rigid.

2. The patient transfer device according to claim 1, wherein the top sheet and the bottom sheet are constructed from at least one of a flexible polymer sheet and a polymer coated fabric.

3. The patient transfer device according to claim 1, comprising a layer of a porous gas distribution material disposed between the top sheet and the bottom sheet.

4. The patient transfer device according to claim 3, wherein the porous gas distribution material defines a thickness of 3 mm or less.

5. The patient transfer device according to claim 3, wherein the top sheet and the bottom sheet are welded directly through the porous gas distribution material disposed between the top sheet and the bottom sheet to form the at least one of spot connections or line connections.

6. The patient transfer device according to claim 5, wherein welding the top sheet and the bottom sheet directly through the porous gas distribution material disposed between the top sheet and the bottom sheet forms a constant amount of material of the gas bearing bladder through which a radiation beam passes.

7. The patient transfer device according to claim 1, wherein the at least one gas inlet comprises at least one of a penetration between the top sheet and the bottom sheet, a penetration through the top sheet, a penetration through the bottom sheet, and a penetration of the at least one of spot connections or line connection between the top sheet and the bottom sheet.

8. The patient transfer device according to claim 1, wherein the at least one of spot connections or line connections between the top sheet and the bottom sheet control at least one of expansion of an inflated thickness of the gas bearing bladder and an airflow pattern through the gas bearing bladder.

9. The patient transfer device according to claim 1, wherein pressurized gas enters the at least one gas inlet through the patient surface.

10. The patient transfer device according to claim 1, wherein the at least one of spot connections or line connections located inside the outer perimeter form one or more inflatable interior regions and one or more inflatable perimeter regions, the inflatable perimeter regions surrounding the inflatable interior regions.

11. The patient transfer device according to claim 10, wherein the inflatable perimeter regions are wider than the inflatable interior regions.

12. The patient transfer device according to claim 10, wherein the inflatable perimeter regions are taller than the inflatable interior regions.

13. The patient transfer device according to claim 10, wherein the bottom sheet of the inflatable interior regions is gas permeable and the bottom sheet of the inflatable perimeter regions is not gas permeable.

14. The patient transfer device according to claim 1, wherein at least one of the top sheet and the bottom sheet is coated with a low friction coating to reduce friction and improve sliding of the gas bearing bladder relative to a supporting surface on which the patient transfer device is positioned.

15. The patient transfer device according to claim 1, comprising one or more tabs attached to and extending around side edges of the gas bearing bladder.

16. The patient transfer device according to claim 1, wherein the gas bearing bladder exhibits an aluminum equivalence of less than 1 mm.

17. The patient transfer device according to claim 1, wherein the gas bearing bladder is removably attached to the patient surface by at least one of an adhesive, a touch fastener, an elastic band, and a button.

18. The patient transfer device according to claim 16, wherein the aluminum equivalence across a surface of the gas bladder has a variation of less than +/−0.25 mm.

19. The patient transfer device according to claim 10, wherein the inflatable perimeter regions increase the stability of the gas bearing bladder relative to a supporting surface on which the patient transfer device is positioned.

20. The patient transfer device according to claim 1, wherein at least one of the top or bottom sheet is removably attached to an exterior of the patient surface with a fastener, the fastener being located below a top surface of the patient surface when the gas bearing bladder is in the attached condition.

21. The patient transfer device according to claim 1, the patient surface including a top surface, a bottom surface, and a side extending between the top surface and the bottom surface, wherein the gas bearing bladder is attached to at least one of the bottom surface and the side of the patient surface.

22. The patient transfer device according to claim 15, wherein the tabs attach the gas bearing bladder to the bottom of the support surface.

23. The patient transfer device according to claim 2, wherein the top sheet and the bottom sheet are constructed from nylon fabric coated with thermoplastic polyurethane.

24. The patient transfer device according to claim 1, wherein the patient surface is x-ray homogeneous.

25. A patient transfer device for transferring a patient onto a target modality, comprising:
a gas bearing bladder, the gas bearing bladder including:
a top sheet and a bottom sheet sealed to each other along an outer perimeter region to form the gas bearing bladder,
at least one gas inlet, wherein the gas bearing bladder has an inflated condition when gas is introduced into the gas bearing bladder through the at least one gas inlet, and wherein the outer perimeter region has a thickness equal to the sum of the thicknesses of the top sheet and the bottom sheet; and
a patient surface configured and dimensioned to support a patient thereon, the patient surface being positioned relative to the gas bearing bladder such that the patient surface is interposed between a patient and the gas bearing bladder, the patient surface being coupled to the gas bearing bladder such that a perimeter of the gas bearing bladder does not extend beyond a perimeter of the patient surface, wherein the patient surface is rigid;
wherein at least one of the top or bottom sheet is removably attached to an exterior of the patient surface with a fastener, the fastener being located below a top surface of the patient surface when the gas bearing bladder is in an attached condition.

26. The patient transfer device according to claim 25, further comprising at least one of spot connections or line connections between the top sheet and the bottom sheet located inside the outer perimeter forming one or more inflatable interior regions and one or more inflatable perimeter regions, the inflatable perimeter regions surrounding the inflatable interior regions,
wherein the bottom sheet of the one or more inflatable interior regions is gas permeable,
wherein the bottom sheet of the one or more inflatable perimeter regions is not gas permeable, and
wherein the inflatable perimeter regions are wider or taller than the inflatable interior regions.

27. The patient transfer device according to claim 25, wherein the top sheet and the bottom sheet are welded directly through a porous gas distribution material disposed between the top sheet and the bottom sheet to form the at least one of spot connections or line connections.

28. The patient transfer device according to claim 25, wherein the gas bearing bladder is removably attached to the patient surface by at least one of an adhesive, a touch fastener, an elastic band, and a button.

29. The patient transfer device according to claim 25, wherein the top sheet is rigid and has a top surface and a bottom surface, and the patient transfer device further comprises at least one of spot connections or line connections located within the outer perimeter region and connecting the bottom sheet to the bottom surface of the top sheet.

30. The patient transfer device according to claim 29, wherein the top surface of the top sheet provides the patient surface.

31. A patient transfer device, comprising:
a gas bearing bladder, the gas bearing bladder including:
a top sheet and a bottom sheet sealed to one another along their outer perimeter relative to each other to form the gas bearing bladder, at least one of the top sheet and the bottom sheet being formed from a flexible material,
at least one of spot connections or line connections connecting the top sheet and the bottom sheet, the spot connections or line connections being located inside the outer perimeter, and
at least one gas inlet,
wherein at least one section of the bottom sheet is gas permeable,
wherein the gas bearing bladder is inflatable from a collapsed condition to an inflated condition when gas is introduced into the gas bearing bladder, the gas bearing bladder having a substantially constant thickness in the collapsed condition to promote x-ray homogeneity of the gas bearing bladder during imaging or treatment; and
a patient surface coupled to the gas bearing bladder such that a perimeter of the gas bearing bladder does not extend beyond a perimeter of the patient surface, the patient surface being configured and dimensioned to support a patient thereon.

* * * * *